United States Patent [19]

Ohara et al.

[11] Patent Number: 5,728,847
[45] Date of Patent: Mar. 17, 1998

[54] METHOD FOR RECOVERING LACTIDE FROM HIGH-MOLECULAR WEIGHT POLYLACTIC ACID

[75] Inventors: Hitomi Ohara, Kyoto; Toshio Okamoto, Hirakata, both of Japan

[73] Assignee: Shimadzu Corporation, Kyoto, Japan

[21] Appl. No.: 713,653

[22] Filed: Sep. 13, 1996

[30] Foreign Application Priority Data

Sep. 14, 1995 [JP] Japan ................. 7-236278

[51] Int. Cl.$^6$ ................. C07D 319/00
[52] U.S. Cl. ................. 549/274
[58] Field of Search ................. 549/274

[56] References Cited

U.S. PATENT DOCUMENTS 4,057,537  11/1977  Sinclair ................. 260/78.3 R

Primary Examiner—Amelia Owens
Attorney, Agent, or Firm—Birch, Stewart, Kolasch & Birch, LLP

[57] ABSTRACT

A method for recovering lactide from a high-molecular weight polylactic acid, comprising the steps of: (a) heat-treating a high-molecular weight polylactic acid to a temperature equal to or higher than a melting point of the polylactic acid to be treated in the presence of a catalyst comprising one or more metals selected from elements of Group IA, Group IVA, Group IVB, and Group VA of the Periodic Table, or compounds thereof; and (b) reducing a pressure to equal to or less than a vapor pressure of lactide at said temperature, to thereby distill and recover the produced lactide.

13 Claims, No Drawings

METHOD FOR RECOVERING LACTIDE FROM HIGH-MOLECULAR WEIGHT POLYLACTIC ACID

BACKGROUND OF THE INVENTION

1. Field of the Invention

The present invention relates to a method for recovering lactide from a high-molecular weight polylactic acid. More particularly, the present invention relates to a method for recovering lactide at high purity mainly from a discarded high-molecular weight polylactic acid.

2. Discussion of the Related Art

A polylactic acid is a biodegradable plastic with significantly low potential of causing environmental hazards. Therefore, it has found a wide range of applications including agricultural or architectural sheets, food wrappings, hygiene materials, fishing nets, fishing lines, and various other purposes.

The polylactic acid may be produced as follows: A cyclic lactide dimer is first synthesized from lactic acids, followed by ring-opening polymerization of the cyclic lactide. Various procedures for synthesizing, purifying and polymerizing lactide are disclosed in U.S. Pat. No. 4,057,537, EP-A-261,572, *Polymer Bulletin*, 14, 491–495 (1985), *Makromol. Chem.*, 187, 1611–1628 (1986), and other chemistry literatures.

In general plastics, such as polyethylene, polypropylene, and polystyrene, resin feeding portions, such as sprues and runners in injection-molding, and both end portions called "selvages" obtained after cutting into a given length of molded products of fibers, sheets, films, and nonwoven fabrics can be reused as starting materials for molding. Also, there has been an increasing social tendency toward recycling of used plastics.

Polylactic acids can be molded by the above methods as used for plastics, and thus leaving sprues, runners, and selvages. Also, some polylactic acids formed by polymerization reaction do not meet the standard requirements. It is highly preferable from the aspect of recycling of resources to recover and reuse polylactic acids formed during molding and production processes as well as used polylactic acids.

However, polylactic acids are highly susceptible to thermal deterioration, and reuse of such materials as they are is liable to cause coloration, degeneration, and decrease in molecular weight of the polylactic acids. Therefore, unlike the above-mentioned general plastics, it is difficult to reuse polylactic acids. Therefore, it has been proposed to depolymerize the subject polylactic acids to reuse the resulting monomers for the polymerization reaction to yield a desired polylactic acid.

For instance, JP-A-7-11044 discloses a method for recovering lactic acid comprising hydrolyzing a polylactic acid. However, in this method, once the polylactic acid is depolymerized back to lactic acid, the resulting lactic acid must be synthesized into lactide before carrying out polymerization to form a polylactic acid. Thus, it is not economically advantageous.

Further, JP-A-63-123401 discloses a method for synthesizing glycolide from a low-molecular polyglycolide using a self-cleanable, twin-screw extruder. However, in this method, the term "low-molecular polyglycolide" refers to those with molecular weights of oligomer region, namely those having weight-average molecular weights of 3,000 or less.

SUMMARY OF THE INVENTION

Accordingly, an object of the present invention is to provide a method for recovering lactide suitable for producing polylactic acids at high purity mainly from a discarded high-molecular weight polylactic acid.

In one aspect, the present invention is concerned with a method for recovering lactide, comprising the steps of:

(a) heat-treating a high-molecular weight polylactic acid to a temperature equal to or higher than a melting point of the polylactic acid to be treated in the presence of a catalyst comprising one or more metals selected from elements of Group IA, Group IVA, Group IVB, and Group VA of the Periodic Table, or compounds thereof; and (b) reducing a pressure to equal to or less than a vapor pressure of lactide at said temperature, to thereby distill and recover the produced lactide.

DETAILED DESCRIPTION OF THE PREFERRED EMBODIMENTS

The present invention will be hereinafter described in detail.

Polylactic acids of mold parts have a weight-average molecular weight of 50,000 to 300,000. The molecular weight is often decreased to about 5000, as the decomposition proceeds in a discarded polylactic acid mold part. In one preferred embodiment, discarded polylactic acid is the target material to be treated with the present invention. Such discarded polylactic acid include, for example, polylactic acid products which do not meet the product requirements; trim scraps including sprue, runner, and selvage; and used polylactic acid products.

Polylactic acids to be treated with the method of the present invention generally have a weight-average molecular weight of from 5,000 to 300,000. Also, the polylactic acids to be treated with the present method include not only a homopolymer of lactic acid, but also copolymers of lactic acid and other lactones, such as β-propiolactone, δ-valerolactone, ε-caprolactone, and δ-butyrolactone, and copolymers of lactic acid and higher alcohols. The method of the present invention may be applied to mixtures of such polylactic acids and other resins.

The catalysts used for the method of the present invention are not particularly limited and any one that can catalyze the depolymerization of a polylactic acid to lactide may be used. Generally, the catalyst used in the present invention is at least one metal selected from the Group consisting of elements of Group IA, Group IVA, Group IVB, and Group VA of the Periodic Table, or a compound thereof.

Examples of the catalysts comprising a metal of group IVA or a compound thereof include organotin compounds, such as tin lactate, tin tartarate, tin dicaprylate, tin dilaurate, tin dipalmitate, tin distearate, tin dioleate, tin α-naphthoate, tin β-naphthoate, and tin octylate; and tin powder.

Examples of the catalysts comprising a metal of Group IA or a compound thereof include hydroxides of alkali metals, such as sodium hydroxide, potassium hydroxide, and lithium hydroxide, weak acid salts of alkali metals, such as sodium lactate, sodium acetate, sodium carbonate, sodium octylate, sodium stearate, potassium lactate, potassium acetate, potassium carbonate, and potassium octylate, and alkoxides of alkali metals, such as sodium methoxide, potassium methoxide, sodium ethoxide, and potassium ethoxide.

Examples of the catalysts comprising a metal of Group IVB include titanium compounds, such as tetrapropyl titanate, and zirconium compounds, such as zirconium isopropoxide.

Examples of the catalyst comprising a metal of group VA include antimony compounds, such as antimony trioxide.

All the above catalysts are conventionally used in the polymerization to give polylactic acids. Among them, catalysts comprising tin or a compound thereof are preferably used in terms of catalyst activity.

The above catalyst is preferably used in an amount of 0.05 to 15% by weight of the polylactic acid to be treated by the present method. When the amount of catalyst is less than 0.05% by weight of the polylactic acid, the amount of the lactide distillate is not sufficient, whereas when the amount of catalyst is higher than 15% by weight, the corresponding increases in distillation speed and amount of lactide distillate are not obtained. More preferred amounts of catalyst are in the range of from 3 to 7% by weight.

In the present invention, lactide is recovered by heating the polylactic acid to a temperature equal to or higher than a melting point of the polylactic acid while reducing a pressure to equal to or less than a vapor pressure of lactide at the above temperature. The melting point of polylactic acids depends on the molecular weight and composition, and it is normally in the range of from about 150° to 180° C. Thus, the heat-treatment is preferably carried out at a temperature of from 170° to 300° C. The pressure is normally reduced by not more than 20 mmHg. Under the above conditions, a polylactic acid is melted to be uniformly mixed with the catalyst, whereby the depolymerization of the polylactic acid is catalyzed to produce lactide. Thus-produced lactide can be gasified and recovered.

When a polylactic acid with a weight average molecular weight of 5,000 to 300,000 is melted at a temperature of 170° to 250° C. and uniformly mixed with a catalyst, it is required to stir the mixture with an extremely strong power. Therefore, the heat-treatment is preferably carried out in a horizontal reactor. For this purpose, any existing reactors for highly viscous fluids can be used. Suitable examples include but are not limited to a horizontal twin-screw extruder, a reactor with a spectacle impeller as manufactured by Hitachi Ltd., Bivolac manufactured by Sumitomo Heavy Industries, Ltd. and an SCR as manufactured by Mitsubishi Heavy Industries, Ltd.

Though the purity of the lactide recovered by the present method is generally high, the lactide may further be subjected to a purification treatment according to necessity before it is used in the polymerization reaction. The methods for purifying lactide are disclosed, for example, in JP-A-6-256340 ("Purification of lactide by melt crystallization"), and JP-A-7-118259 ("Purification and polymerization of lactide"), the disclosures of which are herein incorporated by reference into the present application.

Whether or not the purification treatment is necessary depends on the state of the polylactic acid to be treated. That is, lactide recovered from polylactic acid in the following conditions may sometimes require purification treatment: those with a high moisture content, those stained with impurities, and those to which water is adhered owing to washing. On the other hand, lactide recovered from runners and selvages can be used for polymerization reaction without purification in many cases.

The method of the present invention permits to recover lactide at high purity from a discarded high-molecular weight polylactic acid. The lactide recovered by the present method is suitably reused for polymerization. Therefore, as compared to the method where lactic acid is recovered from polylactic acid, a highly economical recycling of polylactic acid products can be achieved by the present method.

EXAMPLES

The present invention will be further described by means of the following working examples, without intending to restrict the scope of the present invention thereto.

Example 1

Selvages produced upon molding of a polylactic acid film (weight average molecular weight of 150,000) were introduced into a twin-screw extruder (KEXN-30) having 8 barrels made by Kurimoto Ltd. at a rate of 500 g/minute, and tin octylate was added at a rate of 5 g/minute from the third barrel. Vacuuming was performed under a reduced pressure of 15 mmHg from the vents (openings) of the fifth and seventh barrels. At this time, the temperature of the barrels was 200° to 250° C. The gasified lactide was liquefied and recovered using a condenser.

The recovery rate of lactide was 95% based upon the amount of the polylactic acid charged. The lactide recovered showed a high purity of not less than 99%, and could be reused for polymerization.

Example 2

Runners produced upon injection-molding of a polylactic acid (weight average molecular weight of 250,000) were introduced into a twin-screw extruder (KEXN-30) having 8 barrels made by Kurimoto Ltd. at a rate of 500 g/minute, and tin octylate was added at a rate of 25 g/minute from the third barrel. Vacuuming was performed under a reduced pressure of 5 mmHg from the vents (openings) of the fifth and seventh barrels. At this time, the temperature of the barrels was 200° to 250° C. The gasified lactide was liquefied and recovered using a condenser.

The recovery rate of lactide was 93% based upon the amount of the polylactic acid charged. The lactide recovered showed a high purity of not less than 99%, and could be reused for polymerization.

Example 3

The polylactic acid mold (weight average molecular weight of 20,000) which had been produced by injection-molding and was buried in soil for 1 month was washed with water, and introduced into a twin-screw extruder (KEXN-30) having 8 barrels made by Kurimoto Ltd. at a rate of 1,500 g/minute, and tin octylate was added at a rate of 1.5 g/minute from the third barrel. Vacuuming was performed under a reduced pressure of 10 mmHg from the vents (openings) of the fifth and seventh barrels. At this time, the temperature of the barrels was 190° to 230° C. The gasified lactide was liquefied and recovered using a condenser.

The recovery rate of lactide was 85% based upon the amount of the polylactic acid charged. The lactide recovered showed a purity of 95%.

The lactide recovered was purified according to the method described in JP-A-7-118259. Specifically, 200 ml of ethyl acetate and 800 ml of toluene were added to 1 kg of the lactide as recovered, and the mixture was heated to 80° C. After stirring, the mixture was cooled to 4° C. to yield crystalline precipitates. The precipitates were separated by centrifugation at 800 g for 10 minutes, which were then dried at 30° C. in a vacuum drier under a pressure of 5 mmHg for 3 hours to yield purified lactide. The yield was 870 g, and the recovery rate was 87%. The lactide purified showed a high purity of not less than 99%, and could be reused for polymerization.

Example 4

Polylactic acid bottles (weight average molecular weight of 70,000) produced by blow-molding which had been filled with water for 1 month were cut into pieces, and introduced into a twin-screw extruder (KEXN-30) having 8 barrels made by Kurimoto Ltd. at a rate of 1,000 g/minute, and tin octylate was added at a rate of 10 g/minute from the third barrel. Vacuuming was performed under a reduced pressure of 10 mmHg from the vents (openings) of the fifth and seventh barrels. At this time, the temperature of the barrels was 190° to 220° C. The gasified lactide was liquefied and recovered using a condenser.

The recovery rate of lactide was 87% based upon the amount of polylactic acid charged. The lactide recovered showed a purity of 96%.

The lactide recovered was purified according to the method described in JP-A-7-118259. Specifically, the same procedures as in Example 3 were followed, and 910 g of purified lactide was obtained from 1 kg of crude lactide, giving a recovery rate of 91%. The lactide purified showed a high purity of not less than 99%, and could be reused for polymerization.

What is claimed is:

1. A method for recovering lactide from a high-molecular weight polylactic acid, comprising the steps of:
    (a) heat-treating a high-molecular weight polylactic acid to a temperature equal to or higher than a melting point of the polylactic acid to be treated in the presence of a catalyst comprising one or more metals selected from elements of Group IA, Group IVA, Group IVB, and Group VA of the Periodic Table, or compounds thereof; and
    (b) reducing a pressure to equal to or less than a vapor pressure of lactide at said temperature, to thereby distill and recover the produced lactide.

2. The method according to claim 1, wherein said high-molecular weight polylactic acid to be treated in step (a) is a discarded polylactic acid.

3. The method according to claim 1, wherein said high-molecular weight polylactic acid to be treated in step (a) has a weight-average molecular weight of from 5,000 to 300,000.

4. The method according to claim 1, wherein the heat-treatment temperature is from 170° to 300° C.

5. The method according to claim 1, wherein the catalyst is tin or a tin compound.

6. The method according to claim 1, wherein the amount of the catalyst used is from 0.05 to 15% by weight of the polylactic acids to be treated.

7. The method according to claim 1, wherein the heat treatment is carried out in a horizontal, twin-screw reactor.

8. The method according to claim 1, wherein said high-molecular weight polylactic acid to be treated in step (a) is a homopolymer of lactic acid or a copolymer of lactic acid and a lactone selected from the group consisting of β-propiolactone, δ-valerolactone, ε-caprolactone and δ-butryolactone.

9. The method according to claim 5, wherein said tin compound is an organotin compound.

10. The method according to claim 9, wherein said organotin compound is selected from the group consisting of tin lactate, tin tartarate, tin dicaprylate, tin dilaurate, tin dipalmitate, tin distearate, tin dioleate, tin α-naphthoate, tin β-naphthoate and tin octylate.

11. The method according to claim 6, wherein the amount of the catalyst used is in the range of from 3 to 7% by weight of the polylactic acid to be treated.

12. The method according to claim 1, wherein the pressure is reduced by not more than 20 mmHg.

13. The method according to claim 3, wherein said high-molecular weight polylactic acid to be treated in step (a) has a weight-average molecular weight of from 50,000 to 300,000.

* * * * *